US012685661B1

(12) United States Patent
Davis

(10) Patent No.: US 12,685,661 B1
(45) Date of Patent: Jul. 21, 2026

(54) METAL FLANGE FOR AN OSTOMY BAG

(71) Applicant: Michael A. Davis, Canyon Lake, CA (US)

(72) Inventor: Michael A. Davis, Canyon Lake, CA (US)

( * ) Notice: Subject to any disclaimer, the term of this patent is extended or adjusted under 35 U.S.C. 154(b) by 428 days.

(21) Appl. No.: 18/214,901

(22) Filed: Jun. 27, 2023

(51) Int. Cl.
*A61F 5/448* (2006.01)
*A61F 5/44* (2006.01)
*A61F 5/445* (2006.01)

(52) U.S. Cl.
CPC ............ *A61F 5/448* (2013.01); *A61F 5/4405* (2013.01); *A61F 2005/4455* (2013.01)

(58) Field of Classification Search
CPC . A61F 5/448; A61F 5/4405; A61F 2005/4455
See application file for complete search history.

(56) References Cited

U.S. PATENT DOCUMENTS

| | | | | |
|---|---|---|---|---|
| 3,565,073 | A * | 2/1971 | Giesy | A61F 5/449 |
| | | | | 623/66.1 |
| 4,205,678 | A * | 6/1980 | Adair | A61F 5/448 |
| | | | | 604/343 |
| RE32,947 | E * | 6/1989 | Dormer | A61N 1/37223 |
| | | | | 607/57 |
| 5,814,033 | A | 9/1998 | Edwards | |
| 6,520,943 | B1 | 2/2003 | Wagner | |
| 6,537,261 | B1 | 3/2003 | Steer et al. | |
| 6,966,901 | B2 | 11/2005 | Leisner et al. | |

| | | | | |
|---|---|---|---|---|
| 8,142,454 | B2 * | 3/2012 | Harrison | A61B 17/8076 |
| | | | | 606/153 |
| 8,439,915 | B2 * | 5/2013 | Harrison | A61B 17/11 |
| | | | | 606/105 |
| 8,647,304 | B2 | 2/2014 | Axelsson et al. | |
| 9,039,668 | B2 | 5/2015 | Svensby et al. | |
| 9,226,848 | B2 | 1/2016 | Johansson et al. | |
| 9,615,961 | B2 * | 4/2017 | Johansson | A61F 5/445 |
| 9,795,501 | B2 | 10/2017 | Nassopoulos | |
| 10,413,440 | B2 | 9/2019 | Moavenian | |
| 11,103,614 | B2 | 8/2021 | Pearce et al. | |
| 11,129,744 | B2 | 9/2021 | Granet et al. | |
| 12,485,035 | B1 * | 12/2025 | Clingan | A61F 5/448 |
| 2006/0271107 | A1 * | 11/2006 | Harrison | A61B 17/8076 |
| | | | | 606/237 |
| 2007/0276378 | A1 * | 11/2007 | Harrison | A61B 17/70 |
| | | | | 606/309 |

(Continued)

FOREIGN PATENT DOCUMENTS

| | | | | | |
|---|---|---|---|---|---|
| KR | 20260024877 A | * | 2/2026 | | A61F 5/448 |

*Primary Examiner* — Guy K Townsend

(74) *Attorney, Agent, or Firm* — Cramer Patent & Design, PLLC.; Aaron R. Cramer

(57) ABSTRACT

Embodiments of the present disclosure may include an ostomy bag attachment device including an implant mechanism including an outer solid tube. Embodiments may also include an inner mesh tube with a flared flange. Embodiments may also include an inner tissue flange and an outer tissue flange. Embodiments may also include a neodymium magnet ring located on an outer stoma interface. Embodiments may also include a protruding titanium ring on the outer stoma interface. Embodiments may also include a ferrous metal ring located around a bag opening of an ostomy bag. Embodiments may also include a circumferential ostomy flange centrally provided around a stoma.

7 Claims, 7 Drawing Sheets

(56) References Cited

U.S. PATENT DOCUMENTS

| 2009/0048618 | A1 * | 2/2009 | Harrison | ................ | A61B 17/66 |
| | | | | | 600/12 |
| 2015/0128962 | A1 * | 5/2015 | Sinnecker | ............... | A61F 5/449 |
| | | | | | 128/899 |
| 2018/0098876 | A1 * | 4/2018 | Wright | ................... | A61F 5/448 |

* cited by examiner

82

METAL FLANGE FOR AN OSTOMY BAG

RELATED APPLICATIONS

None.

FIELD OF THE INVENTION

The present invention relates generally to a metal flange and more specifically for a metal flange for an ostomy bag.

BACKGROUND OF THE INVENTION

Many persons who suffer from conditions that necessitate surgery that results in an external feces collection device, such as a colostomy or ileostomy, are all too familiar with the hassles and burdens that are connected with the maintenance and upkeep of such devices. These conditions include conditions such as inflammatory bowel disease, diverticulitis, Crohn's disease, and ulcerative colitis. These implements, which are sometimes referred to as ostomy pouches, typically take the form of an object resembling a plastic bag and are secured around the resulting stoma with the aid of adhesive wafers.

Because these wafers use an adhesive that is rather strong, they have a tendency to irritate the skin in the surrounding area. This patch of skin is typically left red, itchy, and possibly much worse after cleansing the area around the stoma, as well as after being exposed to bodily fluids. As a consequence of this, there is a requirement for the development of a technique that allows ostomy bags to be attached while avoiding the drawbacks discussed earlier. The development of the metal flange for an ostomy bag fulfills this need in a manner that is cost-effective and efficient.

SUMMARY OF THE INVENTION

Embodiments of the present disclosure may include an ostomy bag attachment device including an implant mechanism including an outer solid tube. Embodiments may also include an inner mesh tube with a flared flange. Embodiments may also include an inner tissue flange and an outer tissue flange. Embodiments may also include a neodymium magnet ring located on an outer stoma interface. Embodiments may also include a protruding titanium ring on the outer stoma interface. Embodiments may also include a ferrous metal ring located around a bag opening of an ostomy bag. Embodiments may also include a circumferential ostomy flange centrally provided around a stoma.

In some embodiments, the implant mechanism may be used for attaching an ostomy bag to a colostomy, ileostomy, or urostomy. In some embodiments, the implant mechanism may be secured into place using sutures. In some embodiments, the ostomy bag attachment device may include an outer stoma interface that may be sutured to an abdominal wall.

In some embodiments, the outer stoma interface may be attached to an epidermis of an abdominal wall. In some embodiments, the outer stoma interface may include a synthetic silicone elastomer. In some embodiments, the neodymium magnet ring mates with the ferrous metal ring to provide a magnetic attachment between the ostomy bag and the stoma.

In some embodiments, the neodymium magnet ring may be embedded in a synthetic silicone elastomer. In some embodiments, the protruding titanium ring mates with a titanium ring acceptance inlet on the ostomy bag. In some embodiments, the ostomy bag may include a bag opening bordered by the ferrous metal ring. In some embodiments, the implant mechanism provides stabilization within the abdominal wall. In some embodiments, the circumferential ostomy flange provides a fluid-tight seal around the stoma.

Embodiments of the present disclosure may also include a method of implanting an ostomy bag attachment device including the steps of, forming an opening in an abdominal wall. Embodiments may also include attaching a stoma to a flared flange of an implant mechanism using sutures. Embodiments may also include inserting the implant mechanism through the opening and attaching it to the abdominal wall using inner and outer tissue flanges and sutures.

Embodiments may also include attaching an outer stoma interface to the epidermis and mating it to the outer solid tube of the implant mechanism. Embodiments may also include placing a neodymium magnet ring around the opening and securing it in place. Embodiments may also include allowing for post-surgical recovery time before using the ostomy bag attachment device.

In some embodiments, the neodymium magnet ring may be embedded in a synthetic silicone elastomer. In some embodiments, the implant mechanism provides stabilization within the abdominal wall. In some embodiments, the method may include the step of suturing the outer stoma interface to the abdominal wall.

In some embodiments, the ostomy bag may include a ferrous metal ring located around a bag opening. In some embodiments, the method may include the step of mating a protruding titanium ring on the outer stoma interface with a titanium ring acceptance inlet on the ostomy bag. In some embodiments, the ostomy bag attachment device may be implanted during a colostomy, ileostomy, or urostomy procedure. In some embodiments, the circumferential ostomy flange provides a fluid-tight seal around the stoma.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
FIG. 1 is a pictorial view of an ostomy bag attachment device 10, according to the preferred embodiment of the present invention.
Figure 1:
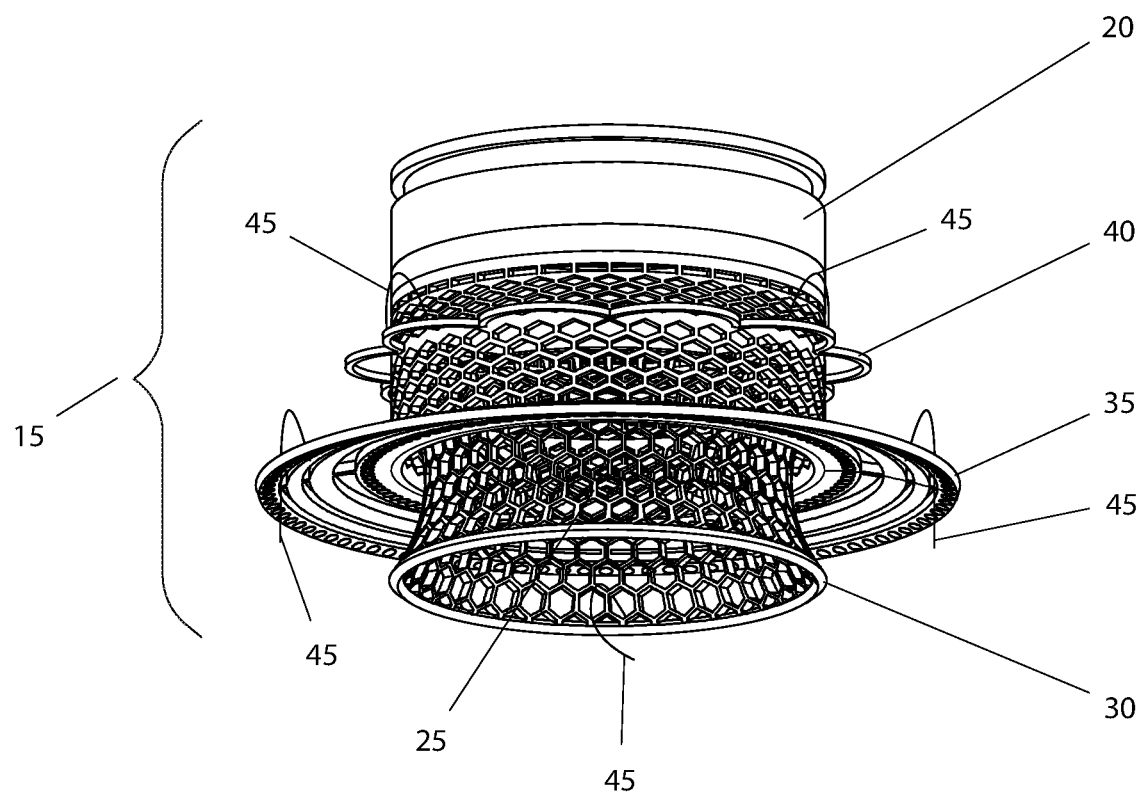

DESCRIPTIVE KEY 10 ostomy bag attachment device
15 implant mechanism
20 outer solid tube
25 inner mesh tube
30 flared flange
35 inner tissue flange
40 outer tissue flange
45 suture
50 stoma
55 opening
60 abdominal wall
65 epidermis
70 dermis
75 subcutaneous tissue
82 outer stoma interface
85 neodymium magnet ring
86 protruding titanium ring
95 patient
100 ostomy bag
105 attachment travel path "a"
110 ferrous metal ring
115 bag opening
120 titanium plate
125 synthetic silicone elastomer
130 ostomy flange
135 titanium ring acceptance inlet

DESCRIPTION OF THE PREFERRED
EMBODIMENTS

The best mode for carrying out the invention is presented in terms of its preferred embodiment, herein depicted within FIGS. 1 through 5. However, the invention is not limited to the described embodiment, and a person skilled in the art will appreciate that many other embodiments of the invention are possible without deviating from the basic concept of the invention and that any such work around will also fall under scope of this invention It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

1. Detailed Description of the Figures

Referring now to FIG. 1, a pictorial view of a device 10, according to the preferred embodiment of the present invention is disclosed. The ostomy bag attachment device (herein also described as the "device") 10, provides for the attachment of an ostomy bag 100 by magnetic means to various types of stomas 50. The device 10 provides for an implant mechanism 15 which is placed during a surgical operation. The implant mechanism 15 may be used during a colostomy procedure, an ileostomy procedure or an urostomy procedure. The teachings of the present invention apply to all three (3) types of ostomies, and while various dimensional and configurational changes may occur to the implant mechanism 15, it should not be interpreted as a limiting factor of the present invention. The implant mechanism 15 includes an outer solid tube 20 which interfaces to other portions of the invention as will be described below. The outer solid tube 20 is in mechanical communication with an inner mesh tube 25 complete with a flared flange 30 which interfaces to the stoma. An inner tissue flange 35 along with an outer tissue flange 40 help to anchor the implant mechanism 15 into place. Various sutures 45 would be used to secure the flared flange 30, the inner tissue flange 35, and the outer tissue flange 40 into position and prevent dislodgment and leaking.

Figure 2:
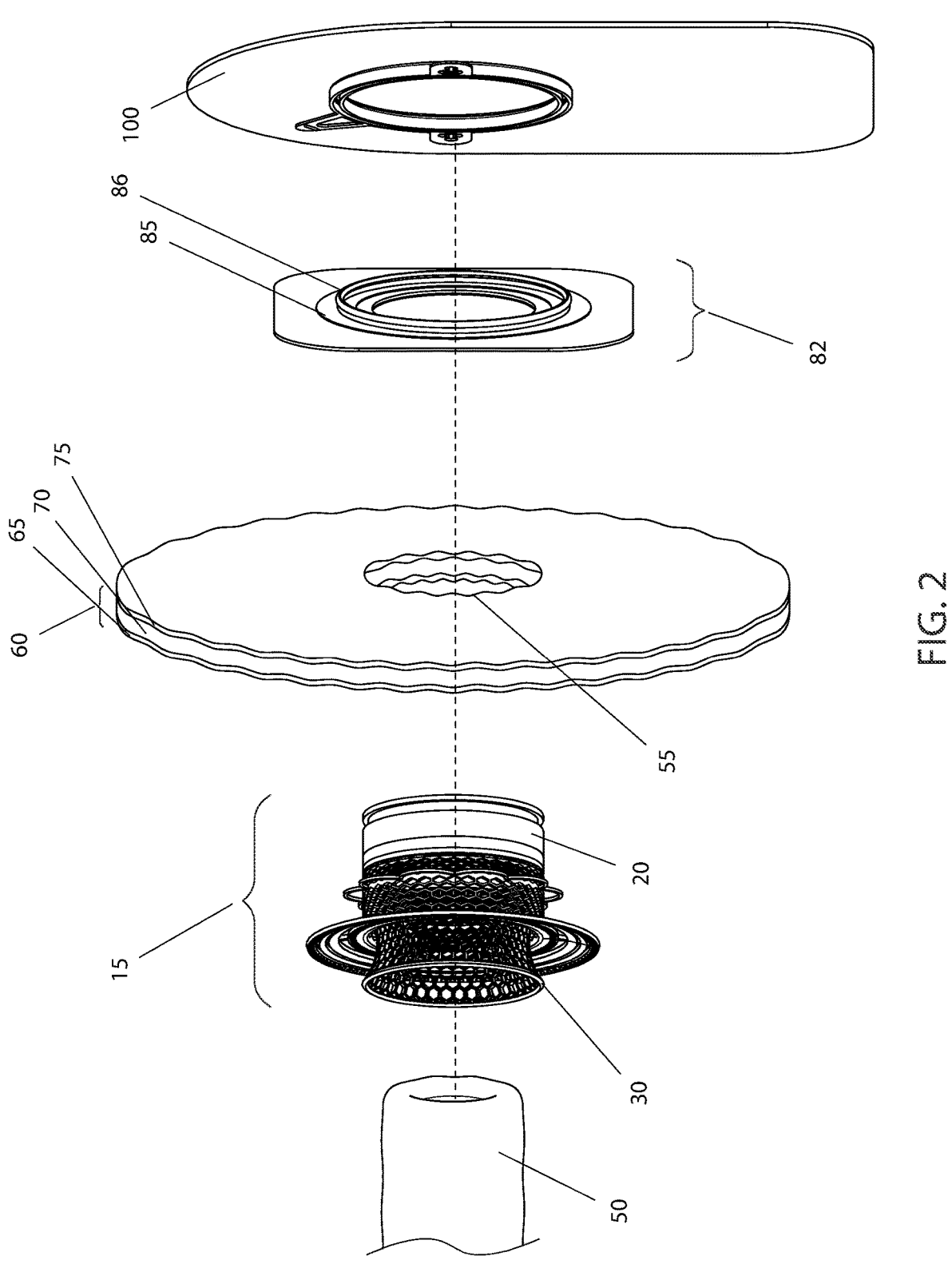
FIG. 2 is an exploded three-dimensional (3D) view of the ostomy bag attachment device 10, according to the preferred embodiment of the present invention.

Referring next to FIG. 2, an exploded three-dimensional (3D) view of the device 10, according to the preferred embodiment of the present invention is depicted. The flared flange 30 of the implant mechanism 15 is attached to a stoma 50 as aforementioned described. The outer solid tube 20 of the implant mechanism 15 passes through an opening 55 in the abdominal wall 60 including at least the epidermis 65, the dermis 70, and the subcutaneous tissue 75. An outer stoma interface 82 is then implanted upon the epidermis 65 of the abdominal wall 60 which remains in place after the surgical implant to protect the epidermis 65 from irritation, inflammation, and infection. The outer stoma interface 82 is sutured to the abdominal wall 60. Next, a neodymium magnet ring 85 is provided as an integral interior component of the outer stoma interface 82. In certain other embodiments, the neodymium magnet ring 85 may be not present. The outer stoma interface 82 is provided with a protruding titanium ring 86 to create a dimple. Further description of the outer stoma interface 82 and associated components will be described in greater detail herein below. The ostomy bag 100 is connected to the outer stoma interface 82.

Figure 3:
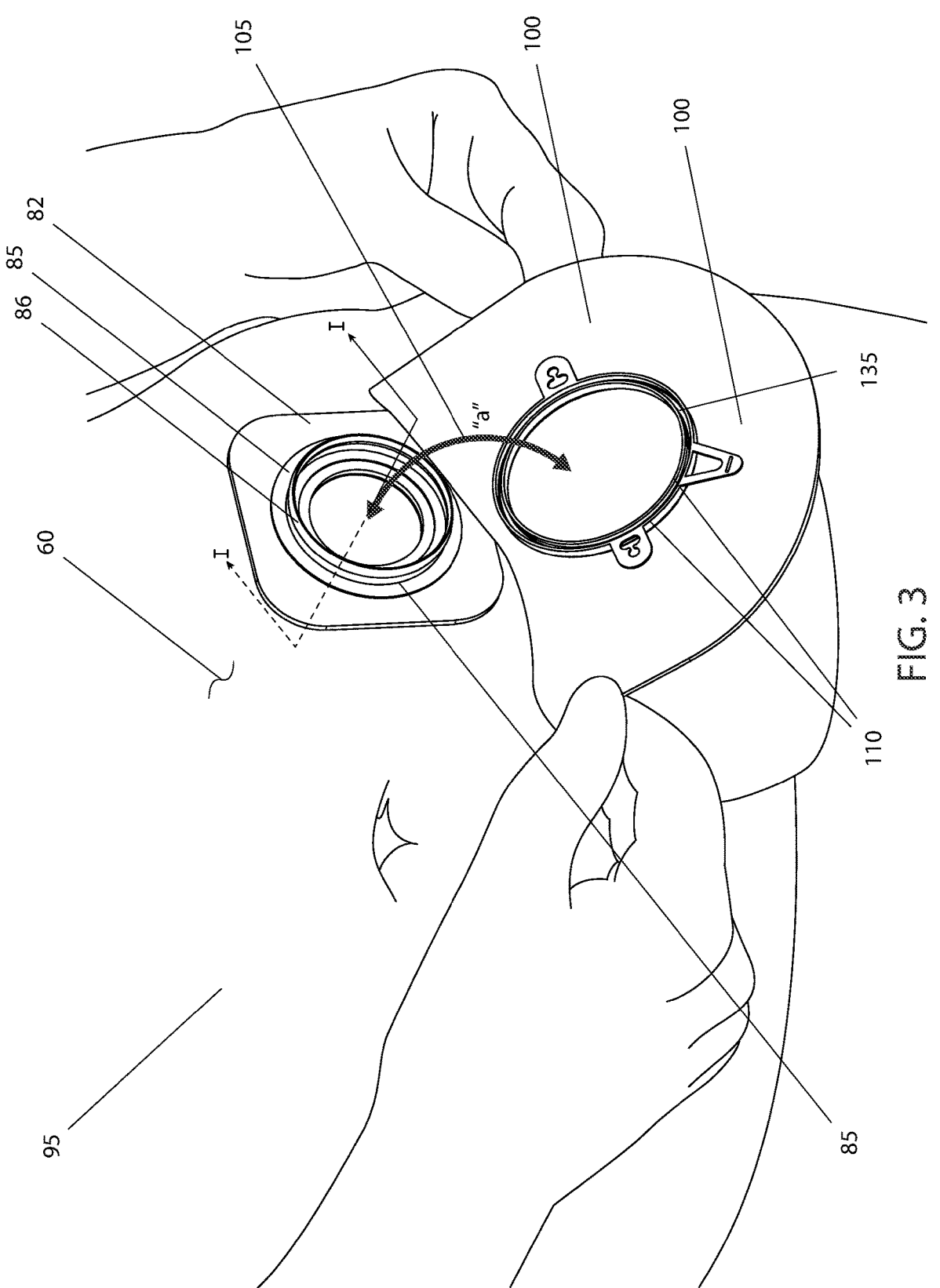
FIG. 3 is a pictorial view of the ostomy bag attachment device 10, shown in an installed state on a patient 95, according to the preferred embodiment of the present invention.

Referring now to FIG. 3, a pictorial view of the device 10, shown in an installed state on a patient 95, according to the preferred embodiment of the present invention is shown. This figure depicts an ostomy bag 100 being applied (or removed) along an attachment travel path "a" 105. The ostomy bag 100 may be provided with a ferrous metal ring 110 that is located around a bag opening 115. The ostomy bag 100 may also be provided with a conventional mechanical connection which is well known in the art. It is envisioned that the patient 95 may decide on having the ferrous metal ring 110 with or without the mechanical connection depending on their personal preferences, daily activities, usage restrictions or the like. As such, the device 10 provides the patient 95 the flexibility of either usage scenario without changes or modification of the outer stoma interface 82.

The outer stoma interface 82 is visible on the abdominal wall 60 of the patient 95 with the neodymium magnet ring 85 depicted via dashed lines due to its hidden state. The neodymium magnet ring 85 then mates with a ferrous metal ring 110 located around a bag opening 115. In a similar manner, the protruding titanium ring 86 mates with a titanium ring acceptance inlet 135 on the ostomy bag 100. In such a manner, the ostomy bag 100 is connected indirectly to the stoma 50 (as shown in FIG. 2), such that bodily wastes can transfer into the ostomy bag 100 through the bag opening 115. The magnetic attachment between the neodymium magnet ring 85 and the ferrous metal ring 110 are viewed as liquid and gas tight and is structurally significant to prevent unintentional dislodgement. The ostomy bag 100 may be removed when overpowered by direct hand strength applied by the user along the attachment travel path "a" 105.

Figure 4:
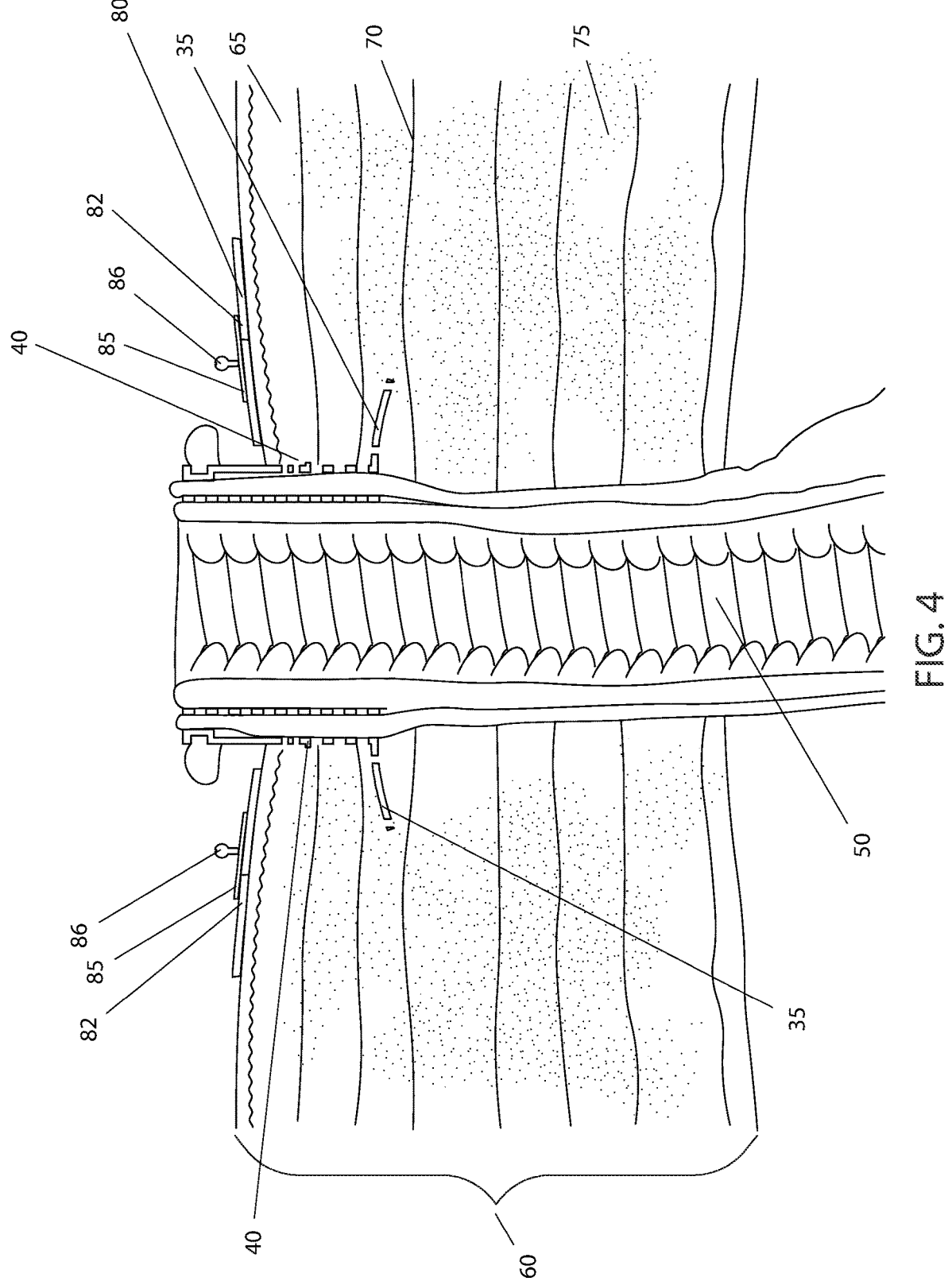
FIG. 4 is a sectional view as seen along a line I-I, as shown in FIG. 1, according to the preferred embodiment of the present invention.

Referring next to FIG. 4, a sectional view as seen along a line I-I, as shown in FIG. 1, according to the preferred embodiment of the present invention is disclosed. This figure provides detailed knowledge of the device 10 as it passes through the abdominal wall 60. The outer stoma interface 82, with the contained neodymium magnet ring 85 and the protruding titanium ring 86 is secured against the epidermis 65 layer of the abdominal wall 60 using well-known skin implant methods. The stoma 50 is attached to the flared flange 30 and as it heals, attaches to the inner mesh tube 25. The inner tissue flange 35 and the outer tissue flange 40 are attached into the abdominal wall 60 and provide stabilization within the epidermis 65, the dermis 70, and the subcutaneous tissue 75.

Figure 5:
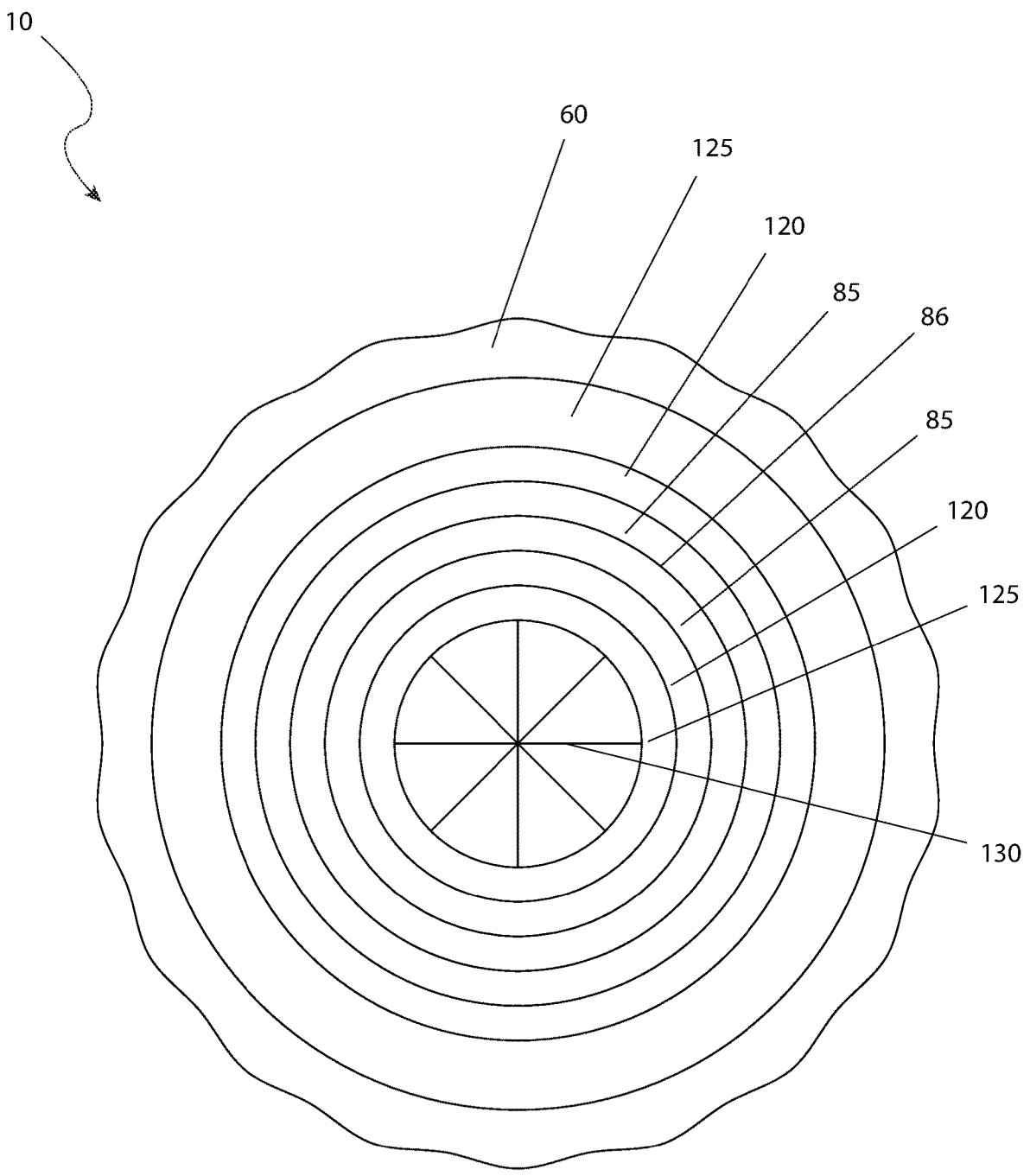
FIG. 5 is a sectional view of the as seen along a line II-II, as shown in FIG. 2, according to the preferred embodiment of the present invention.

Referring to FIG. 5, a sectional view as seen along a line II-II, as shown in FIG. 2, according to the preferred embodiment of the present invention is depicted. The neodymium magnet ring 85 (if present) will be anchored to the titanium plate 120. In turn, the titanium sheet will be embedded in a synthetic silicone elastomer 125. It is noted that the titanium plate 120 and the neodymium magnet ring 85 are provided as an integral part of the synthetic silicone elastomer 125 and remain visible but are in a flush or recessed state. The surgical procedure would implant the outer stoma interface 82 around the stoma 50 of the patient 95 (as shown in FIG. 3), as well as to an abdominal wall 60. This configuration provides for a thin titanium plate 120 or sheet with the protruding titanium ring 86 extending through the neodymium magnet ring 85. The neodymium magnet ring 85 is attached to the titanium plate 120 and reinforces the already secure connection provided by the protruding titanium ring 86. The synthetic silicone elastomer 125 encases the outer portions of the titanium plate 120 while leaving the protruding titanium ring 86 and the neodymium magnet ring 85 exposed. Similarly, the outer portion of the neodymium magnet ring 85 is inlaid in the synthetic silicone elastomer 125. The outer magnetic portion is wider and located slightly above the synthetic silicone elastomer 125. The distal portion of the protruding titanium ring 86 will allow the ostomy bag 100 (as shown in FIG. 3) to clip into place, with the neodymium magnet ring 85 surrounding the protruding titanium ring 86. A circumferential ostomy flange 130 is centrally provided around the stoma 50 (as shown in FIGS. 3 and 4).

Figure 6:
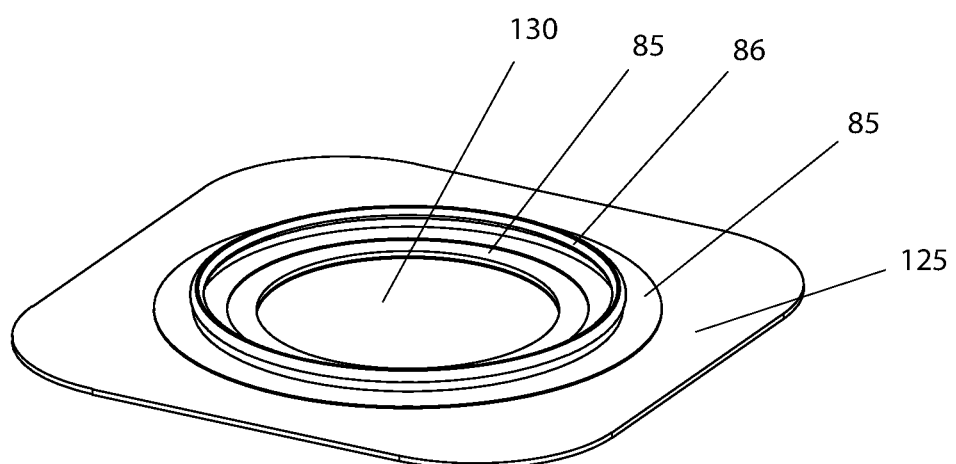
FIG. 6 is a perspective view of the outer stoma interface 82 as used with the ostomy bag attachment device 10, according to the preferred embodiment of the present invention; and, FIG. 7 is a perspective view of the ostomy bag 100 as used with the ostomy bag attachment device 10, according to the preferred embodiment of the present invention.

Referring next to FIG. 6, a perspective view of the outer stoma interface 82 as used with the device 10, according the preferred embodiment of the present invention is disclosed. The outer stoma interface 82 provides for the synthetic silicone elastomer 125 around the distal perimeter. The neodymium magnet ring 85 is located on both the inner and outer lower surfaces of the protruding titanium ring 86. As aforementioned described, the circumferential ostomy flange 130 remains centrally located.

Figure 7:
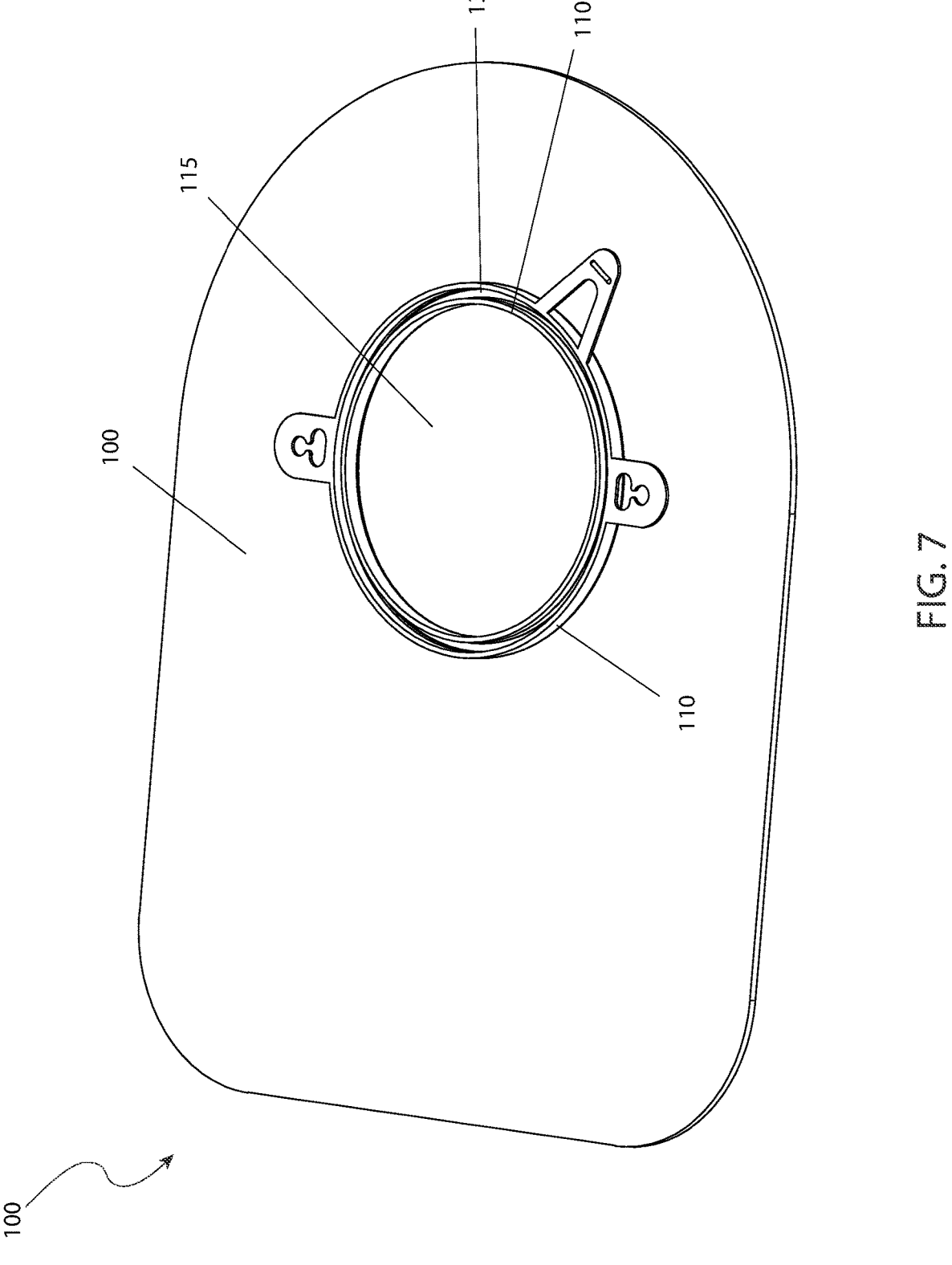

Referring to FIG. 7, a perspective view of the ostomy bag 100 as used with the modified 10, according the preferred embodiment of the present invention is depicted. The ostomy bag 100 is provided with the expected bag opening 115. The bag opening 115 is bordered by the ferrous metal ring 110. It is noted that the ferrous metal ring 110 is bisected by the titanium ring acceptance inlet 135 which accepts the protruding titanium ring 86 (as shown in FIG. 6).

It is appreciated that the geometry and materials associated with the design, manufacture, and use of the device 10 is desirably suitable and configured for providing a connection with other, conventional designs and styles of ostomy bags 100 and provide fluid communication with a stoma 50. Such ostomy bags 100 may not process magnetic connection means.

2. Operation of the Preferred Embodiment

The preferred embodiment of the present invention can be utilized by the common user in a simple and effortless manner with little or no training. It is envisioned that the device 10 would be constructed in general accordance with FIG. 1 through FIG. 5. The device 10 would be procured from medical supply houses and implanted by a surgical team during a surgical operation. Special attention would be required with the size of the device 10, type of ostomy to be performed, and other medical considerations.

Once procured and all pre-surgical considerations have been addressed, the device 10 would be implanted in the following manner: an opening 55 is formed in the abdominal wall 60; the stoma 50 would be pulled through the abdominal wall 60 and attached to the flared flange 30 of the implant mechanism 15 using sutures 45; the implant mechanism 15 would then be inserted through the opening 55 and attached to the abdominal wall 60 via the inner tissue flange 35 and the outer tissue flange 40 using sutures 45; the outer stoma interface 82 would be attached to the epidermis 65 and mated to the outer solid tube 20; and, if present, the neodymium magnet ring 85 is placed around the opening 55 and secured in place with the medical grade silicone 90. After an appropriate amount of post-surgical recovery time, the device 10 is ready for use. A similar process would be used with the alternate embodiment of FIG. 5, with a reduction of steps needed as the titanium plate 120 and the neodymium magnet ring 85 are embedded within the synthetic silicone elastomer 125.

During utilization of the device 10, the following procedure would be initiated: an ostomy bag 100 with a ferrous metal ring 110 around the bag opening 115 would be applied to outer stoma interface 82 along the attachment travel path "a" 105 while mating the ferrous metal ring 110 with the neodymium magnet ring 85, if present. This allows the stoma 50 to pass bodily waste into the ostomy bag 100 in an airtight manner. Should the ostomy bag 100 become full, or otherwise required emptying, the patient 95 would grasp the ostomy bag 100 and overcome the power of the neodymium magnet ring 85 attachment to the ferrous metal ring 110, thus allowing the ostomy bag 100 to be disposed of or otherwise emptied in a responsible manner. An empty ostomy bag 100 would be attached in a reverse manner in an otherwise repeating process. A similar process would be used with conventional ostomy bags 100 not equipped with the ferrous metal ring 110.

As such, the device 10 provides for a unique and novel approach to securing ostomy bags 100 during use. Conventional ostomy bags 100 rely on a disposable adhesive wafer made of plastic that adheres to the skin around the stoma 50 on the abdominal wall 60 of the patient 95. The device 10 uses a similar mechanical connection method but is not disposable and does not rely on adhesive. The connection means that the ostomy bag 100 connects to is made of titanium in the shape of a protruding titanium ring 86 that is inlaid into a synthetic silicone elastomer 125 that is sutured onto the abdominal wall 60 and connected to the circumferencing ostomy flange 130, that is directly around the stoma 50, thus preventing any stool from coming in contact with the patient's actual dermis 70. The materials of construction along with its increased durability and longevity in application is markedly different than currently available methods or products. The device 10 allows patients 95 to utilize conventional ostomy bags 100 with adhesive, or ostomy bags 100 with a ferrous metal ring 110 to facilitate quick and easy attachment and removal while reducing leakage and associated mess and fuss.

The features of the device 10 provide the following benefits: the protection from infection on skin from being in contact with stool; the elimination of the need to apply any adhesives to the skin which damages skin in itself from prolonged adhesion or skin allergies; the elimination of the need for an ostomy wafer which is currently attached to any bag to your stomach; the disposing of ostomy bags 100 would be made possible with an ostomy bag 100 that has a ferrous metal ring 110 that allows it to attach to the neodymium magnet ring 85; and, the enablement of an ostomy bag 100 with a disposal bag that can allow a patient 95 to dispose of the ostomy bag 100 when necessary in a sanitary way.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. An ostomy bag attachment system comprising:
an implant mechanism configured to be inserted around a stoma, the implant mechanism comprising:
    an outer solid tube configured to be positioned around the stoma and distal to epidermis of abdominal wall;
    an inner mesh tube inside of and integral with the outer solid tube and comprising a flared flange and configured to be positioned around the stoma and within the epidermis and dermis of the abdominal wall; and
    an inner tissue flange integral with the inner mesh tube and configured to be positioned around the stoma and within the dermis of the abdominal wall; and
    an outer tissue flange integral with the inner tissue flange and distal to the inner tissue flange and configured to be positioned around the stoma and within the epidermis of the abdominal wall;

an outer stoma interface forming a circumferential ostomy flange centrally provided around a stoma configured to be positioned adjacent to the epidermis and around the outer solid tube around a stoma, the outer stoma interface comprising:
    a stoma opening configured to be positioned around the outer solid tube around a stoma;
    a synthetic silicone elastomer flange comprising a flange stoma opening and configured to be sutured to an epidermis of an abdominal wall surrounding the stoma to align the stoma opening with the flange stoma opening;
    a neodymium magnet ring embedded in the synthetic silicone elastomer flange and adjacent to an outer surface of the epidermis; and
    a protruding titanium ring attached to the neodymium magnet rind and extending distal to and substantially perpendicular to the neodymium magnet ring;
a ferrous metal ring a attached around the bag opening of the ostomy bag and configured to be magnetically attached to the protrudin titanium ring to seal the ostomy bag to the outer stoma interface and the distal surface of the outer stoma interface.

2. The ostomy bag attachment system of claim 1, wherein the ostomy bag is configured to be used as a colostomy bag, an ileostomy bag, or a urostomy bag.

3. The ostomy bag attachment system of claim 2, wherein the implant mechanism is secured into place within the epidermis and/or the dermis using sutures.

4. The ostomy bag attachment system of claim 1, wherein the neodymium magnet ring magnetically mates with the ferrous metal ring to provide a magnetic attachment between the ostomy bag and the stoma.

5. The ostomy bag attachment system of claim 1, wherein the protruding titanium ring magnetically mates with a titanium ring acceptance inlet adjacent to the ferrous metal rind of the ostomy bag.

6. The ostomy bag attachment system of claim 1, wherein the implant mechanism provides stabilization within the abdominal wall.

7. The ostomy bag attachment system of claim 1, wherein the circumferential ostomy flange provides a fluid-tight seal with the epidermis around the stoma.

\* \* \* \* \*